United States Patent [19]

Gerstel et al.

[11] 3,964,482

[45] June 22, 1976

[54] DRUG DELIVERY DEVICE

[75] Inventors: Martin S. Gerstel; Virgil A. Place, both of Palo Alto, Calif.

[73] Assignee: Alza Corporation, Palo Alto, Calif.

[22] Filed: May 17, 1971

[21] Appl. No.: 144,061

[52] U.S. Cl. .............................. 128/260; 128/253; 128/216; 128/213
[51] Int. Cl.² ........................................ A61M 7/00
[58] Field of Search ........... 128/260, 268, 215, 216, 128/253, 213, 2 W, 2 R, 1 R, 329, 330, 333, 314, 315

[56] References Cited
UNITED STATES PATENTS

| | | | |
|---|---|---|---|
| 946,837 | 1/1910 | Common ............................. | 128/260 |
| 1,485,126 | 2/1924 | Schumacher ....................... | 128/260 |
| 1,699,012 | 1/1929 | Naylor .......................... | 128/333 UX |
| 2,196,379 | 4/1940 | Bender ................................ | 128/260 |
| 2,670,489 | 3/1954 | Cross .................................. | 128/260 |
| 3,053,255 | 11/1962 | Meyer ................................. | 128/268 |
| 3,466,131 | 9/1969 | Arcudi ............................ | 128/260 X |
| 3,598,122 | 10/1971 | Zaffaroni ............................ | 128/268 |
| R25,637 | 9/1964 | Kravitz et al. ...................... | 128/253 |

FOREIGN PATENTS OR APPLICATIONS

1,133,709  4/1957  France ................................ 128/260

*Primary Examiner*—Aldrich F. Medbery
*Attorney, Agent, or Firm*—Thomas E. Ciotti; Paul L. Sabatine; Edward L. Mandell

[57] ABSTRACT

A drug delivery device for percutaneously administering a drug comprising a plurality of projections, a drug reservoir containing a drug, and where the projections extend from the reservoir and are adapted for penetrating the stratum corneum for percutaneously administering a drug from the reservoir to produce a local or systemic physiological or pharmacological effect.

1 Claim, 7 Drawing Figures

INVENTORS
Martin S. Gerstel
Virgil A. Place
BY Steven D. Goldby +
Paul L. Sabatine
Attorneys

DRUG DELIVERY DEVICE

BACKGROUND OF THE INVENTION

1. Field of the Invention

This invention relates to a new and useful drug delivery device. Specifically, the invention concerns a drug delivery device for administering a drug to achieve a local or systemic physiological or pharmacological effect wherein the device comprises a plurality of projections for penetrating the stratum corneum of the epidermis, and a reservoir containing a drug in immediate proximity with the projections for supplying a drug for percutaneous administration through the stratum corneum penetrated by the projections.

2. Description of the Prior Art

A long felt need existed in the medical art, prior to this invention, for a drug delivery device for use in the percutaneous administration of a drug. This need existed because the art lacked a device for percutaneously administering a drug at a programmed rate of drug administration to achieve a particular drug level in the circulatory system for a preselected period of time, and also because the art lacked a device for percutaneously administering a drug that essentially overcame the skin' natural barrier to penetration by bacterial, chemical or other external substances. The skin'S barrier to penetration stems from both its morphological and marcomolecular organization Morphologically, the composite epithelial layer of the skin, also called epidermis, is the part of the skin endowed with the barrier against penetration, and it consists of four layers. These layers are an outermost layer called stratum corneum and three underlying layers called stratum granulosum, stratum malpighii and stratum germinativum. The stratum corneum is a heterogenous layer of flattened, relatively dry, keratinised cells with a dense underlying layer commonly called the horny layer. In the past, it was generally held that this horny layer acted as the barrier to the penetration of external substances into the body. *J. Invest. Dermat.*, Vol 50, pages 19 to 26, 1968. Now, it is generally held that the whole stratum corneum and not a discrete cellular layer functions as a barrier to the penetration of substances into the body. The whole stratum corneum is held to be a barrier because of a chemical keratin-phospholipid complex that exists in the stratum corneum and acts along with the horny layer as a barrier to the penetration of substances into the body. For this invention, the whole stratum corneum is considered as the natural barrier to penetration. *J. Invest. Dermat.*, Vol 50, pages 371 to 379, 1968; and, ibid, Vol 56, pages 72 to 78, 1971.

The stratum corneum, which is about 15 microns thick when dry and about 48 microns thick when fully hydrated, acts as a barrier for an extremely large variety of compounds. The barrier holds for compounds with large molecular volumes, for compounds substituted with functional groups, for small soluble molecules, for non-electroytes, and the like. *J. Invest. Dermat.*, Vol 52, pages 63 to 70, 1969. Once a compound is made to pass through the stratum corneum, for example, by surgically stripping the stratum corneum, there is no major hindrance to penetration of the remaining epidermal layers or the dermis. After this, the compound enters into the circulation via the capillaries. *Progress in the Biological Sciences in Relation to Dermatology*, 2nd Ed., pages 245, 1964, Univ. Press, Cambridge; and, *J. of Drug and Cosmetic Ind.*, Vol 108, No. 2, pages 36 to 39 and 152 to 154, 1971.

In view of the above presentation, once a drug has penetrated through the stratum corneum, with the aid of the drug delivery device of the invention, penetration through the remaining layers of the skin proceeds readily. Absorption of a drug into the stratum corneum with no further penetration is considered retention and not percutaneous penetration. The passage of the drug into local or systemic circulation is considered as a further or continuing result of percutaneous penetration of drug administered according to this invention. As used herein, the term "percutaneous" means penetration through the skin to the local or systemic circulatory system by puncturing, scraping, or cutting the stratum corneum but not puncturing, scraping, or cutting to a substantial extent, the interior layers of the skin.

Those skilled in the art will appreciate that drug retention, as discussed above, is usually achieved by using devices known as scarifiers or vaccinating instruments. These instruments and their results are significantly different from the drug delivery device of this invention and its results. For example, scarifiers and like instruments usually scarify, that is, they scratch or make small cuts or an area for vaccination as reported in *Webster's Seventh New Collegiate Dictionary*, 1969, page 769; and, *Stedman's Medical Dictionary*, 1966, page 1728. These instruments are used by the medical art for a single, quick, application of a massive dose of vaccine and they are not used by the medical arts as a drug delivery device for the controlled and prolonged administration of effective amounts of a drug for local therapy or systemic therapy. Representative of prior art sacrifiers and vaccinating instruments are U.S. Pat. No. 2,947,787 which discloses a bubble containing a biological fluid and an injector with prongs of 1 to 10 millimeters in length for rupturing the bubble and for applying a single, topical application of the fluid; U.S. Pat. No. 2,893,392, disclosing an envelope containing a biological liquid and an injector with prongs of 1 to 5 millimeters for penetrating the envelope, scarifying the skin and applying a single dose of vaccine thereto; U.S. Pat. No. Re. 25,637 illustrating a capsule and a serrated scarifier for dispensing a vaccine and scratching the skin with the same instrumentality; and U.S. Pat. Nos. 3,123,212; 2,522,306; 3,351,059, and the like that disclose scarifiers with prongs of at least 150 microns in length for making superficial incision in the skin for applying a vaccine thereto. Thus, as taught by the prior art, these instruments have a single, immediate use while the drug delivery device of this invention can be designed for the continual, prolonged, controlled release of a drug to produce a local or systemic effect. Also, the projections of the drug delivery device of this invention are designed to penetrate the stratum corneum for the administration of a drug without contacting the body nerves for achieving an essentially painless drug administration.

Objects of the Invention

Accordingly, in view of the above presentation, it becomes an immediate object of this invention to make available to the art a novel and useful device for penetrating the stratum corneum for administering a drug through the stratum corneum.

Another object of the invention is to provide a drug delivery device having a means for perforating the stratum corneum for administering a drug percutaneously from a drug reservoir embodied within the drug delivery device.

Still yet another object of the invention is to provide a drug delivery device having hollow skin puncturing projections with an aperture for percutaneously administering a drug through the hollow members from a drug source.

Yet still another object of the invention is to provide a drug delivery device comprising stratum corneum puncturing projections for percutaneously administering a drug from a drug source by diffusing a drug from the source and through the puncturing projections.

Another object of the present invention is to provide a novel article of manufacture for penetrating mammalian skin for enhancing drug administration therethrough to achieve local therapy or systemic therapy.

Another object of the invention is to provide a drug delivery device comprising projections for penetrating the stratum corneum, a reservoir containing a drug and a membrane interposed between the projections and the reservoir for the program release of a drug from the reservoir to the projections.

Another object of this invention is to provide a drug delivery device for the continuous administration of controlled amounts of drugs through the stratum corneum for prolonged periods of time to achieve local therapy or systemic therapy.

Yet still another object of the present invention is to provide a low cost drug delivery device for use in the percutaneous administration of a drug.

These objects, as well as other objects, features and advantages will become more readily apparent from the following detailed description, the drawings, and the accompanying claims.

SUMMARY OF THE INVENTION

This invention concerns a drug delivery device for use in the percutaneous administration of a drug for local therapy or systemic therapy. The device generally comprises a reservoir containing a drug, and a multiplicity of puncturing projections extending from at least a part of the reservoir's surface and wherein the projections are adapted for perforating the stratum corneum of the skin to enhance percutaneous drug administration. In the drug delivery device of the invention, the projections and the reservoir can be constructed as a unit piece or the projections and the reservoir can be fabricated from parts into the drug delivery device.

BRIEF DESCRIPTION OF THE DRAWINGS

In the accompanying drawings, which are not drawn to scale but rather to emphasize the puncturing projections.

In the drawings and the specification, like parts in related figures are identified by like number. The terms appearing earlier in the specification and in the description of the drawings, as well as embodiments thereof, are further described elsewhere in the disclosure.

DETAILED DESCRIPTION OF THE DRAWINGS

Figure 1:
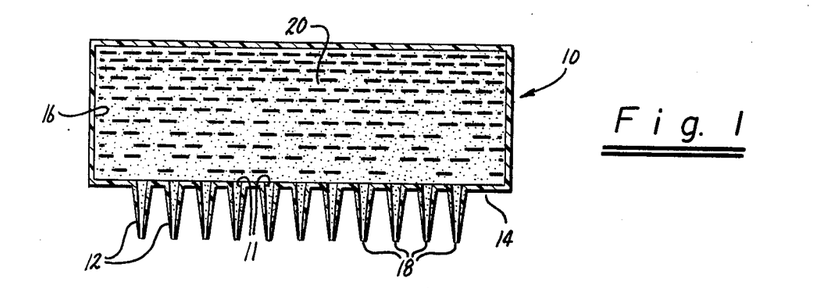
FIG. 1 is a schematic cross-sectional view illustrating a drug delivery device of unit construction made according to the invention.

Turning now to the drawings in detail, one embodiment of the new drug delivery device is generally indicated in FIG. 1 by the number 10. Device 10 is a single piece device comprising a plurality of projections 12 extending outwardly from one surface 14 of a drug reservoir 16 and it is made from a polymer material or the like. Projections 12 are fabricated in this embodiment in a needle-like design, that is, hollow or with a passageway for a drug 20 and with the free end of the projections having a wall defining an opening or aperture 18 of a preselected size and shape. The projection's end extending from the drug reservoir also has an opening 11 for the passage of the drug 20. Reservoir 16 contains the drug or a solution of drug 20 in communication with the passageway within each projection 12. Projections 12 are adapted to puncture and penetrate the stratum corneum of the epidermis and to administer drug 20 from the drug reservoir 16 into the body by percutaneous absorption. In operation, when device 10 is applied to the stratum corneum, projections 12 penetrate the stratum corneum for the passage of a drug 20 from the reservoir 16 through the passageway in projections 12 and through apertures 18 where drug 20 is administered beneath the stratum corneum.

Figure 2:
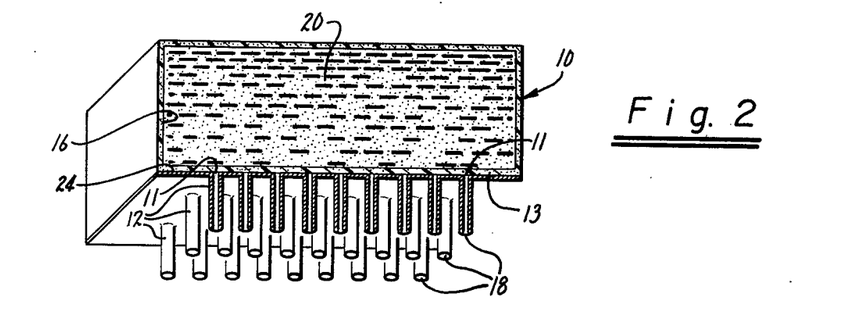
FIG. 2 is a bottom elevational fragmentary view depicting a drug delivery device with a plurality of hollow apertured pointed projections extending from a drug source.

FIG. 2 illustrates another drug delivery device of the invention. In FIG. 2, a drug delivery device 10 is shown formed of two separate parts that when suitably joined together act in concert to function as a single piece drug delivery device. One part of this two part drug delivery device 10 is comprised of a plurality of puncturing projections 12 constructed from a thin metal, alloy or polymer base 24 with the projections extended outwardly from the exposed surface of base 24. Projections 12 usually are round and formed with a passageway and a sharp opening 28 at their free end. The end of projections 12 at base 24 also are made with an opening 11 for permitting a drug 20 to pass from drug reservoir 16 into passageway of projections 12. The other part of the two part drug delivery device 10 is drug reservoir 16 positioned and over-layed on base 24. Drug reservoir 16 generally is made from a moldable polymer in the form of a hollow container, a solid, or the like and it is held on base 24 by molding the reservoir on the base or it is held on the base by an adhesive layer interposed on the peripheries between the base and reservoir. Drug reservoir 16 wall 13 over-layed on base 24 is optionally formed with openings (not shown) in axial alignment with openings 11 of projections 12, or alternatively wall 13, as shown, is made of a material permeable to drug 20, as by diffusion, to release drug from the reservoir to the projections at a predetermined, controlled rate. Thus, drug 20 contained in drug reservoir 16 can be in communication with the passageway of projections 12 through openings in wall 13 or through a barrier of a drug release rate controlling material.

Figure 3:
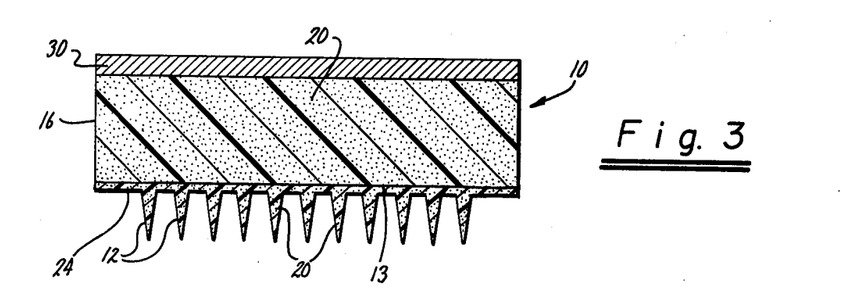
FIG. 3 is another schematic cross-sectional enlarged view illustrating another embodiment of the drug delivery device made with a backing member.

FIG. 3 illustrates another drug delivery device of the invention. In FIG. 3, a drug delivery device 10 is shown comprising a drug reservoir 16 containing a drug 20, a base 24 positioned on one face surface of the reservoir and consisting of a plurality of puncturing projections 12 that extend outwardly from the exposed surface of base 24, and a backing member 30 positioned on the face surface of the reservoir distant from base 24. Backing member 30 also can be placed on the side walls of reservoir 16, which is advantageous if the walls are permeable to drug 20, as this prevents drug loss from reservoir 16. In this embodiment, reservoir 16 is illustrated as being a matrix having drug 20 distributed therethrough and being permeable to passage of the drug by diffusion. Base 24 and projections 12 are made of a drug release rate controlling material, permeable to passage of the drug 20, and act to regulate the rate of passage of drug 20 diffusing from reservoir 16 to projections 12. Drug entering projections 12 diffuses through their length. Thus, the drug delivery device of this embodiment functions through the drug release rate controlling base to percutaneously administer drug 20 at a precisely controlled rate to the puncturing projections for administration through the stratum corneum.

Figure 4:
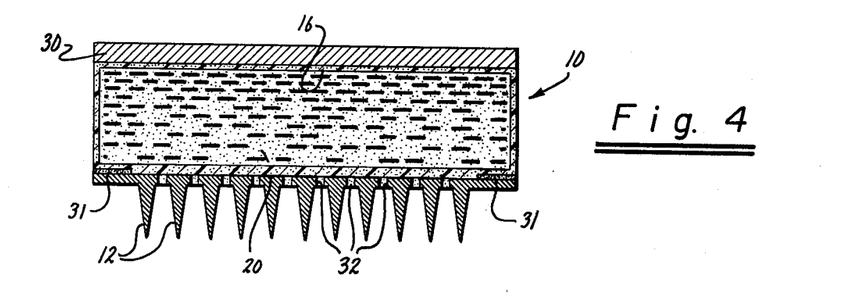
FIG. 4 shows a side view of an embodiment of a drug delivery device of a plurality of projections fixedly mounted onto a drug reservoir.

Turning now to FIG. 4 there is illustrated another embodiment for administering drug through the stratum corneum. As seen in FIG 4, a drug delivery device 10 is comprised of a drug reservoir 16 that contains a drug, a solution of drug, or a solid pharmaceutical composition containing a drug 20, and a backing member 30 on one face surface of drug reservoir 16. While this embodiment illustrates a device with a backing member, it is to be understood that the backing member is optional for this and other embodiments of the device. Reservoir 16 wall distant from backing member 30 is made of a drug release rate controlling material, permeable to drug as by diffusion, to control the flow of drug from reservoir 16. This wall bears thereon an adhesive layer 31 for maintaining a multiplicity of puncturing projections 12 that act as a means for effecting passage of drug from reservoir 16 through the stratum corneum. Projections 12 are formed from a single piece of material adapted to overlie an area of skin and they are sufficiently sharp for puncturing the stratum corneum of the skin. The projections can be hollow or solid and in this embodiment they are illustrated as solid projections, impermeable to passage of drug 20. Projections 12 can be made to touch each other at their origin (not shown) or they can be formed with an aperture 32 spaced between each projection for enhancing the movement of drug 20 released from reservoir 16 about the outer surface of projections 12. In this device, a drug is administered at a controlled rate of release from reservoir 16 through its drug release rate controlling wall, to flow through apertures 32 and then along the outer surface of projections 12 and through the stratum corneum to achieve local or systemic therapy.

Figure 5:
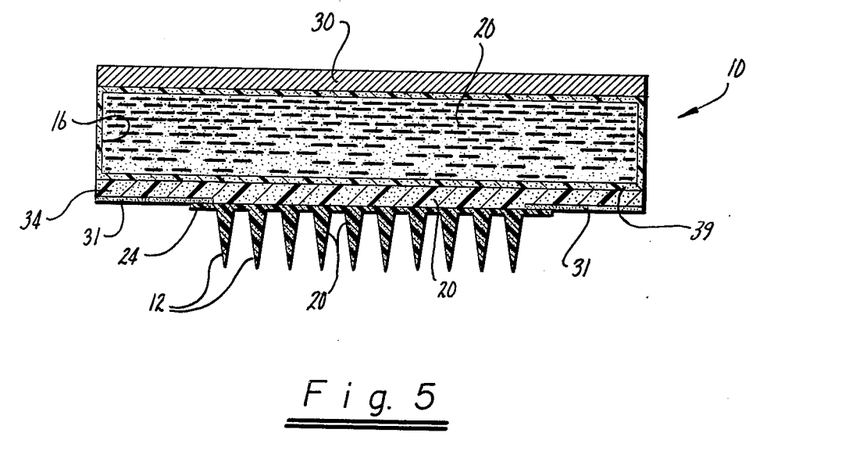
FIG. 5 illustrates a drug delivery device of a plurality of projections and a reservoir with a membrane, for controlling the rate of release from the reservoir, interposed between the projections and the reservoir.

FIG. 5 illustrates another drug delivery embodiment of the invention. In this embodiment, a drug delivery device 10 is comprised of a drug reservoir 16 that contains a drug 20 and has a wall 39 optionally formed with (1) an aperture (not shown) or mulitplicity of apertures of varying dimensions defining a passageway or passageways through wall 39 to permit drug to flow therethrough, or (2) formed of a drug release rate controlling material, as shown, permeable to passage of drug as by diffusion to meter the flow of drug from the reservoir. A membrane 34, also formed of a drug release rate controlling material, is carried by wall 39. The purpose of membrane 34 is two fold; first to meter drug release from reservoir 16 when wall 39 is formed with apertures, and secondly, to cooperate with wall 39 when it is formed of a material permeable to drug for achieving a precise control of drug release from reservoir 16. A base member 24 consisting of a multiplicity of puncturing projections 12 is carried on the surface of membrane 34 distant from wall 39. Base member 24 and puncturing projections 12 can be made from a material permeable to the passage of drug 20, as shown, with the projections extending from the base. Alternatively, the projections can be hollow and formed with a wall or walls of a material that is permeable to the passage of drug and whose wall or walls define an internally disposed space within the projections, that is empty, or filled with a liquid such as water, a hydrogel or the like. Base member 24 and puncturing projections 12 can also be formed from a single piece of stainless steel, vitallium, or a polymer with the projections fabricated as round, hollow needles with openings at both ends, usually with the opening distal from the base beveled for facilitating essentially painless penetration through the stratum corneum for administering a drug released by membrane 34 through the stratum corneum. An optional, pressure sensitive adhesive layer 31 usually is charged on the outer periphery of membrane 34 and it is provided for positioning the device on the skin during administration and to give a releasable grip between the device and the skin. The device also can have a backing member 30 that is adapted for over-lay on the surface of the reservoir distant from projections 12. The backing member can also be placed on the remaining free surfaces of reservoir 16 and its purpose is to prevent unwanted passage of the drug through the surfaces of the reservoir, especially when the reservoir is made from a material permeable to drug. An auxillary purpose of the backing member is to provide support for the device.

Figure 6:
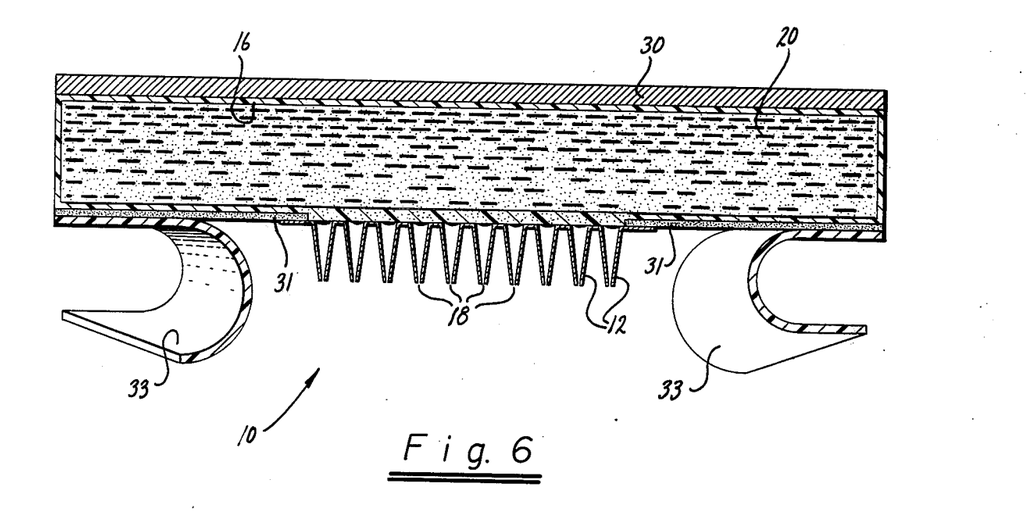
FIG. 6 is a schematic cross-sectional view illustrating another embodiment of the drug delivery device with the puncturing projections and reservoir integral with a supporting member for holding the device on the skin.

In FIG. 6, there is illustrated another embodiment of the invention. In FIG. 6, a drug delivery device 10 is comprised of a drug reservoir 16 containing one or more drugs 20 and bearing on one of its surfaces a backing member 30. The surface of reservoir 16 distant from backing member 30 is formed of a drug release rate controlling material and bears thereon a thin layer of an adhesive 31 that serves three purposes: first, it positions a plurality of stratum corneum puncturing projections 12 with openings 18 on the reservoir; second, it provides a means for releasably affixing the device to the skin; and third, it holds a bandage cover 33 on the device for maintaining the integrity of the device when it is not in use. In use, the bandage cover is stripped from the device before the device is applied to the skin.

Figure 7:
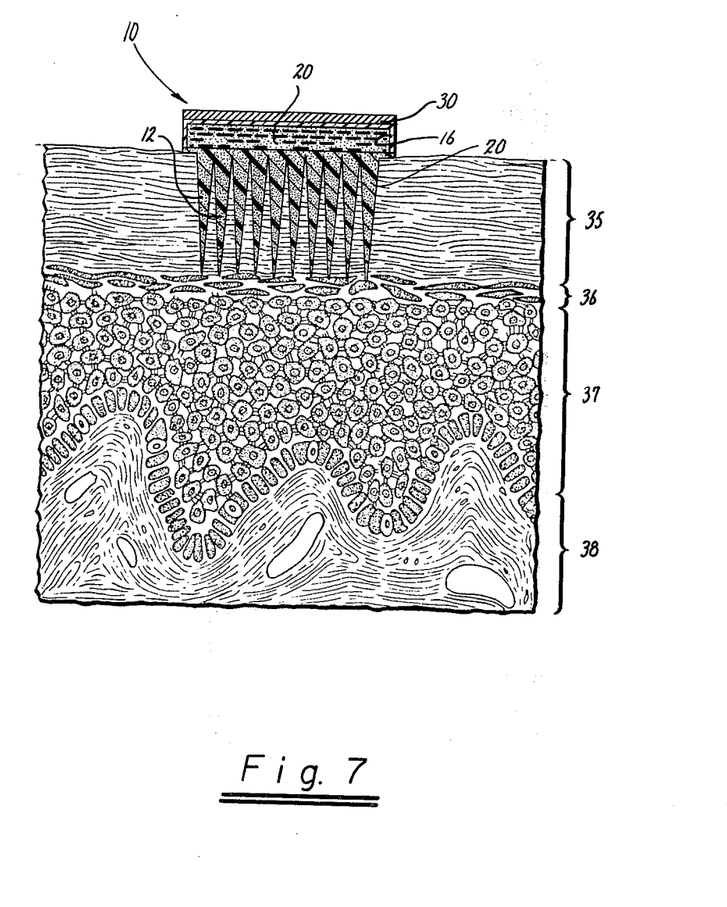
FIG. 7 is a diagrammatic illustration of one embodiment of the drug delivery device placed on the skin with the projections penetrating the stratum corneum for percutaneously administering a drug.

The accompanying drawing, FIG. 7, is presented to further facilitate an understanding of the invention. In FIG. 7, a drug delivery device 10, generally fabricated according to the description presented in describing FIGS. 1 to 6 inclusive, is comprised of backing member 30, a drug reservoir 16 containing a drug 20 and puncturing projections 12 containing drug 20, is shown in a drug administration position. The drug delivery device is illustrated with its puncturing projections 12 piercing the natural, outer layer of the epidermis, the stratum corneum 35. As mentioned above, the major barrier properties of the skin, such as resistance to penetration, reside with the stratum corneum. The inner division of the epidermis generally comprises three layers commonly identified as stratum granulosum 36, stratum malpighii 37 and stratum germinativum 38. Once the drug is administered beneath the stratum corneum, there is essentially little or no resistance to penetration or to absorption through the stratum granulosum, stratum malpighii and stratum germinativum for absorption and circulation of drug into the body.

DETAILED DESCRIPTION OF THE INVENTION

In accordance with this invention, a multiplicity of projections 12 for puncturing the stratum corneum are present on one face surface of the drug delivery device in any predetermined arrangement, for example, as a cluster of projections spaced in rows having any desired number, or in any spaced apart relation of one projection to each other. As used herein, the term "puncturing projections" includes any projections adapted to puncture, penetrate, scrape or cut the stratum corneum. The projections can be of any geometric shape and diameter that lends itself to be made into projections, such as needles, spikes, tines, pointed triangles, pointed cones, pyramidal points, hollow or solid, with or without an opening at one or at both ends thereof, and the like. The projections are usually at any angle that corresponds to the angle of the body skin. Generally, the projections are at an angle of approximately 90° to the surface of the reservoir, but they can be disposed at any angle that will facilitate penetration of the stratum corneum. The projections can exist, as mentioned above, in any pattern and they are usually about 0.5 mm to 5 mm apart. The projections are fabricated with a width or diameter that facilitates penetration of the stratum corneum for achieving administration of a drug. The upper limit is governed by the width or diameter which can conveniently penetrate the stratum corneum and the lower limit is governed by limitations on manufacturing projections of extremely fine diameter for penetrating the stratum corneum. Generally, the dimensions of the projections will correspond to the standard medical gauge needle dimensions, such as 15 gauge through 40 gauge and the like. The projections can also have the dimensions that correspond to other standard gauge needles, such as standard insulin needles, immunization needles, and the like. The height of the projections is subject to variation that corresponds to the natural thickness of the stratum corneum, for one of the principal features of the invention is that the projections are to penetrate the stratum corneum without penetrating interior layers of the skin and without contacting the nerves of the skin. Usually, the projections will be about 5 microns to about 100 microns in length, with the length for most applications being about 10 to 20 microns, 20 to 40 microns, or about 30 to 50 microns, generally 20 microns.

Puncturing projections 12 can be fabricated as hollow projections with openings at both ends to function as a conduit for the flow of drug from the reservoir through the stratum corneum. When the projections are hollow with openings at their ends, it is advantageous to block the free ends of the projections prior to use (as by cover 33 in FIG. 6) to prevent premature drug release. In addition, the projections can be hollow but with no openings at their distal ends. In this case, they are formed of a material permeable to passage of the drug at a controlled rate so that drug entering the projections from the reservoir is administered through the stratum corneum by passage through the walls of the projections. Such projections can be filled with a liquid, hydrogel, sol, gel or the like for transporting a drug through the projections and through the stratum corneum. The projections can also be formed of a solid material permeable to passage of the drug, in which projections the drug is carried from the reservoir through the stratum corneum by diffusion of the drug through the projections at a programmed rate of drug administration. When it is desired to form the projections of a soft drug release rate controlling material, the projections can be reinforeced with wires or needles to facilitate puncturing of the stratum corneum. Also, whether the projections are hollow or solid, drug released from the reservoir at a programmed rate can be carried through the stratum corneum by flowing along the exterior surface of the projections.

The puncturing projections 12 and base 24, as described above, can be made from a wide variety of materials. One class of suitable materials is polymers and the polymeric derivatives thereof. The polymers acceptable for forming puncturing projections of solid design (which carry drug along their exterior surface) or projections made with a passageway and openings at both ends are materials characterized by properties such as a high degree of impact strength, good hardness, resistance to deformation, good tensile strength, does not adversely effect the drug or the host, and readily lend themselves to forming puncturing projections for penetrating or piercing the stratum corneum. Examples of materials include, acrylonitrile-styrene copolymers; acetal homopolymers and copolymers; acrylics; methyl methacrylics; phenolics; melamine fomaldehyde resins; poly(ethylene terephthalate); acrylonitrile and methacrylonitrile polymers and copolymers thereof; cross-linked alkyl and aryl silicone polymers; polycarbonates; halogenated vinyl chloride polymers and copolymers; phenylene oxide condensation polymer; poly(sulfone) resins; aliphatic and aromatic polyamides and polyimides; and the like. Puncturing projections 12 and base 24 of this design can also be made from other materials such as metals and alloys. Examples of metals and alloys include stainless steel; tungsten steel; manganese steel; tantalum; titanium alloys consisting of nickel, molybdenum and chromium; vitallium alloys consisting of cobalt, chromium and molybdenum; and the like.

The puncturing projections 12 and drug reservoir 16 of drug delivery device 10 that comprise a single piece drug delivery device are formed by art known methods for processing plastics, such as injection molding, compression and transfer molding, and the like. In one embodiment the device is made by first mixing plastic pellets or powders and a drug and then feeding the mixture into a heated barrel of a molding machine. Next, after the plastic drug mixture softens, it is conveyed by the thrust of a ram into a template comprising a mold of predetermined design of projections and reservoir where the plastic drug mixture cools and forms to give drug delivery device. The puncturing projections 12 and base 24 of a two part device are made by standard manufacturing techniques, before they are joined to a reservoir. The projections and base are made, for example, from a polymeric material that can be processed by molding, thermoforming, deep drawing, injection, extrusion coating, laminating, and like techniques. In forming the puncturing projections by these techniques, for example, in the thermoforming process a sheet of plastic is softened by heat until pliable and then forced by air pressure against a cold mold surface where the plastic sheet cools and retains the projection shape of the mold. In the deep drawing technique, a sheet of polymer is warmed sufficiently to be readily deformable and a plurality of vacuum retaining cups are used to draw therein the polymer to form the puncturing projection means. The just described techniques manufacture puncturing projections that are hollow to permit a drug from the reservoir to enter into the projections to travel and diffuse through the material into a host. The techniques also are used to make projections 12 extending from base 24. The puncturing projections can also be made by these techniques with a small aperture at the tips of the puncturing projections for increasing the rate of drug administration into a host. The puncturing projections when solid are easily formed by molding, casting, coating and laminating into molds, and the like. The puncturing projections when made of metals or alloys are generally made by conventional needle drawing, single or multiple punching operations, stamping, forging, and the like techniques. For example, in one embodiment a plurality of puncturing projections is formed in a punching operation from a thin strip of metal, for example, stainless steel, with a die to first punch out the metal, and then bending the punched metal outwardly from the plane of the strip to form sharply pointed, shaped puncturing projections.

Drug reservoir 16 can comprise various forms and shapes such as hollow, solid, laminated and the like, and it is made from material that does not adversely effect the drug. The reservoir can be made, as described above and as illustrated in FIG. 1, in open flow communication with the puncturing projections to permit a drug to flow to the puncturing projections. The reservoir can also be made, separate from the projections, as described above and illustrated in FIG. 2, with a wall having openings that function to meter the release of drug from the reservoir to the puncturing projections when the openings and the projections are in axial alignment with each other. Alternatively, the reservoir can be separated from the projections by having a wall that acts as a barrier and is made of a drug release rate controlling material, such as a polymeric membrane, as illustrated in FIGS. 2 through 7, that functions to control thr rate of passage or release of drug from the reservoir to the projections.

The reservoir can have various shapes and structures and it can be formed by standard manufacturing techniques. For example, in one embodiment, the reservoir can be molded into the form of a hollow container with one or more drugs contained therein and it can have one wall fabricated with openings for metering the flow of drug from the reservoir to the projections, or it can have a wall of a drug release rate controlling material to regulate the flow, as by diffusion, of a drug through the wall to the puncturing projections. The reservoir can also be made in the form of an envelope formed from laminae of polymeric material permeable to the passage of the drug enclosed therein, with the laminae nearest the puncturing projections acting as a rate controlling barrier to regulate the flow of drug from the reservoir to the projections. The envelope can be made of many laminae of like polymeric structure or the laminae may be of unlike polymeric structure, with the laminae nearest the puncturing projections regulating the flow of drug from the reservoir to the projections.

The reservoir also can be made of double layer films of like or unlike chemical and physical structure with the drug dispersed throughout one, or more than one of the films. The walls of this reservoir, as with a hollow container or the like, can be of any thickness, and the thickness will depend on the nature of the reservoir and the drug contained therein. Usually, the reservoir wall will have a thickness of from 0.001 millimeters to 10 millimeters thick, or the like. Another embodiment of the invention comprises a reservoir of a solid matrix housing the drug distributed therethrough, as illustrated in FIG. 3. The manufacture of this embodiment is accomplished by adding to the matrix material the drug in solid or liquid form and subsequently converting the matrix to a solid by curing, cooling and the like. The drug can also be distributed in the matrix by immersing the solid matrix in the drug to effect diffusion of the drug into the matrix. Additionally, the drug in the reservoir can be present in other forms, for example, a fluid colloidal form as a sol, a colloid in a more solid form than a sol, such as a gel, and the like. Thus, the reservoir of the drug delivery device of the invention, whether integrally formed with the puncturing projections or independently formed and suitably fixed to the puncturing projections, serves as a drug container for supplying drug to the puncturing projections. When the drug in the reservior is in open flow communication with the projections, the drug release rate is governed by passage through the projections. Alternatively, when the reservoir wall is of a drug release rate controlling material, the drug is metered through the reservoir wall with its rate of passage controlled by composition, fabrication design, and thickness of the reservoir wall adjacent to the projections, for percutaneous administration by the puncturing projections of the drug delivery device.

Generally, the reservoir is made from synthetic or naturally occurring polymeric materials, including those described above as being suitable for forming the projections 12 and base 24 and those described hereinafter as being drug release rate controlling.

As described above with reference to the drawings, projections 12, base 24, wall 13 of reservoir 16, wall 39 of reservoir 16, and/or membrane 34 can be formed of a drug release rate controlling material. Such materials are permeable to passage of the drug at a controlled, predetermined rate, by diffusion of drug through the material or by passage of drug through microscopic pores in the material. Exemplary drug release rate controlling materials are polymers such as poly(ethylene); poly(propylene); poly(tetrafluoroethylene); poly(vinyl chloride); poly(vinylidene chloride); chloride); poly(chlorotrifluorethylene); poly)isobutylene); poly(acrylonitrile); poly(vinylpyrrolidone); poly(ethylene terephthalate); poly(vinyl alcohol); poly(vinyl) methyl ether); poly(vinyl acetate); sodium(polystyrene (polystyrene sulfonate); and the like.

Representative of copolymers of various compositional proportions having drug release rate controlling properties are, by way of non-limited example, copolymers such as vinyl chloride copolymer with a compositional range of 92 to 8 to 50 to 50; vinylidene chloride acrylonitrile composition of 92 to 8 and 80 to 20; vinylidene chloride-acrylonitrile-vinyl chloride of 75 to 80/10/10 to 15; vinylidene chloride isobutylene of 70 to 30; vinyl chloride acrylonitrile copolymer; vinyl chloride diethyl fumariate copolymer; acrylonitrile vinyl acetate copolymer; vinylidene chloride vinyl chloride copolymer 40/60 and 10/90; vinylidene chloride acrylontrile copolymer 60/40 and 12/88; vinyl chloride acrylonitrile copolymer 80/20, 75/25, 50/50 and the like, styrenemaleic anhydride copolymers; vinyl chloride butyl-α-chloroacrylate; polyethylene vinyl acetate; and the like.

Another class of suitable drug release rate controlling materials include the organopolysiloxanes, also known as silicone rubbers. These rubbers include the conventional heat curable silicone rubbers and ambient temperature vulcanizable silicone rubbers. The silicone rubbers include those which are converted to the rubbery state by the action of heat and are predominantly linear organopolysiloxanes characterized by an average degree of substitution of about two organic groups attached directly to silicone per silicon atom. Generally, the organic groups are monovalent hydrocarbon radicals such as alkyl, aryl, alkenyl, alkaryl, aralkyl and the like; as exemplified by methyl, phenyl, vinyl radicals and the like. Variations of the organic groups in the silicone rubber can be used to vary the solubility of the drug in the polymer and hence it can control the speed of migration of the drug through the polymer. Typical examples include poly[di(alkyl siloxanes], such as poly[dimethylsiloxane], copolymers such as methylphenyl and dimethylpolysiloxane, and the like.

The room temperature vulcanizable silicone rubbers are also commercially available and known to the art. In general, they employ the same silicone polymers as mentioned above although the polymers often contain a greater amount of silicon bonded hydroxy groups. This type of silicone rubber cures at room temperature in the presence of catalysts, such 2-ethylheoxate, di-(2-ethyhexyl) adipate, stannous methyl adbietate and the like. Exemplary methods for preparing silicone rubbers are set forth in U.S. Pat. Nos. 2,541,137; 2,723,966; 2,863,846; 2,890,188; 2,927,907; 3,002,951; and 3,035,016.

Another class of drug release rate controlling materials are the hydrophilic polymers of monoesters of an olefinic acid, such as acrylic acid, methacrylic acid, and the like. Exemplary polymers of this class include poly(hydroxyethylacrylate) and poly(hydroxyyethylmethacrylate) and the like. The acrylate polymers are commercially available and their preparation is described in U.S. Pat. Nos. 2,976,576; 3,220,960; Belgian Pat. No. 701,813, and the like. When using these hydrophilic polymers, the drug is often dissolved in a solvent such as a lower alcohol to promote passage of the drug through the polymer.

The rate of passage of a drug through a drug release rate controlling material is usually influenced by factors such as the structure of the materials, its degree of saturation, the presence of cross-linking, the solubility of the drug in the material, the thickness of the material, and the like. Thus, selection of particular drug release rate controlling materials will be dependent on the particular drug to be administered. The rate of drug diffusion through different drug release rate controlling materials can easily be ascertained by standard techniques known to the art as recorded in *J. Pharm. Sci.*, Vol 52, pages 1145 to 1149, 1963; ibid, Vol 53, pages 798 to 802, 1964; ibid, Vol 54, pages 1459 to 1464, 1965; ibid, Vol 55, pages 840 to 843 and 1224 to 1239, 1966; *Encyl. Polymer Sci. Technol.*, Vols 5 and 9, pages 65 to 82 and 794 to 807, 1968; the references cited therein, and the like.

The reservoir, as above described, can be joined to the puncturing projections, for example, as in FIGS. 2 through 7, by art known methods, such as by forming, molding, curing, and cooling the reservoir on the puncturing projections or the base, or by adhesively joining the reservoir to the puncturing projections or to the base. The reservoir can be joined to the puncturing projections, or to the base, or to the membrane (34 in FIG. 5) by adhesively joining the periphery of the reservoir thereto to permit the drug to travel from the reservoir to the puncturing projections without passing through the adhesive. The adhesive also can be applied to the total interface surface between the projections and the reservoir, the surface between the reservoir and membrane, the surface between the membrane and projections, and between reservoir and base in a thin layer to permit drug migration therethrough according to the practice of this invention. Exemplary adhesives include acrylic polymers such as esters of acrylic acid with alcohols such as n-butanol, n-pentanol, iso-pentanol, 2-methyl butanol, 1-methyl methyl butanol, 3-methyl pentanol, and the like. the copolymers can also be used, as copolymerized with ethylenically unsaturated monomers such as acrylic acid methacrylic acid, acrylamide, methacrylamide, N-alkoxymethyl acrylamides, N-alkoxymethyl methacrylamides, itaconic acid, vinyl acetate, N-branched alkyl meleamic acids wherein the alkyl group has 10 to 24 carbon atoms, glycol diacrylates, or mixtures of these; elastomeric silicone polymers; polyurethane elastomers, rubbery polymers such as polyisobutylene, polyisoprene; cellulose derivatives such as ethyl cellulose, methyl cellulose, carboxymethyl cellulose and the like; natural gums such as guar, acacia, pectins and the like. Generally, an adhesive layer about 0.001 mils to 10 millimeters or more in thickness can be used to join the reservoir to puncturing projection, or to the base, or for interposing a membrane there-between to fabricate the drug delivery device for percutaneously administering a drug.

In the manufacture of the drug delivery device 10 as in FIGS. 1 through 7 inclusive the device can be fabricated with a backing member or backing strip. The backing member when optionally used serves to limit the passage of the drug through the surfaces of the reservoir not in contact with the puncturing projections, when the reservoir is permeable to drug passage by diffusion, and it also serves to provide support for the reservoir and the puncturing projections. Additionally, the backing member can act as a means for applying manual pressure to the drug device for guiding the puncturing projections through the stratum corneum for administering the drug into the host. The backing member can be a single layer of material, a multi-layer of materials, it can be in the form of precast films, fabrics, and other types of laminae that are bonded or joined to the reservoir by heat, adhesive, curing the reservoir on the backing, coating onto the reservoir, and by like techniques. Generally, the backing member can be of any thickness, for example, 0.001 millimeters to 10 millimeters or more and its thickness will usually correspond to the dimensions of the reservoir, or the drug device it is affixed thereto. The backing member can be flexible or nonflexible and exemplary materials include cellophane; cellulose acetate; ethylcellulose; plasticized vinylacetate-vinylchloride copolymers; poly(ethylene terephthalate); nylon; poly(ethylene; poly(vinylidene chloride); vinylidene chloride-vinyl chloride copolymer 92/8; vinylidene chloride-acrylonitrile copolymer 80/20; chlorotrifluoroethylene; coated flexible fibrous backings such as nonporous paper; cloth; aluminum foil; and the like.

In the specification and the accompanying claims, the term "drug" broadly includes physiologically or pharmacologically active substance for producing a localized or systemic effect or effects in mammals including humans and primates; avians; valuable domestic household, sport or farm animals; or for administering to laboratory animals such as mice, rats, guinea pigs; and the like. That is, the novel drug delivery device can be used for administering drugs that are physiologically or pharmacologically active at a point in near relation to the drug delivery device, or, for administering a systemically active substance which will produce a physiological or pharmacological response at a site remote from the point of application of the drug delivery device. The active agents that can be administered by the novel device include, without limitation, for example, drugs acting on the central nervous system such as, hypnotics and sedatives such a pentobarbital sodium, phenobarbital, secobarbital, thiopental, etc; heterocyclic hypnotics such as dioxopiperidines, and glutarimides; hypnotics and sedatives such as amides and ureas exemplified by diethylisovaleramide and α-bromoisovaleryl urea and the like; hypnotics and sedative alcohols such as carbomal, naphthoxyethanol, methylparaphenol and the like; and hypnotic and sedative urethans, disulfanes and the like; psychic energizers such as isocarboxazid, nialamide, phenelzine, imipramine, tranylcypromine, pargylene and the like; tranquilizers such as chloropromazine, promazine, fluphenazine reserpine, deserpidine, meprobamate, benzodiazepines such as chlordiazepoxide and the like; anticonvulsants such as primidone, diphenylhydantoin, ethotoin, pheneturide, ethosuximide and the like; muscle relaxants and anti-parkinson agents such as mephenesin, methocarbomal, trihexylphenidyl, biperiden, levo-dopa, also known as L-dopa and L-α-3-4-dihydroxyphenylalanine, and the like; analgesics such as morphine, codeine, meperidine, nalorphine and the like; antipyretics and anti-inflammatory agents such as asperin, salicylamide, sodium salicylamide and the like; local anesthetics such as procaine, lidocaine, naepaine, piperocaine, tetracaine, dibucaine and the like; antispasmodics and antiulcer agents such as atropine, scopolamine, methscopolamine, oxyphenonium, papaverine, prostaglandins such as $PGE_1$, $PGE_2$, $PGF_{1\alpha}$, $PGF_{2\alpha}$, PGA and the like; anti-microbials such as penicillin, tetracycline, oxytetracycline, chlorotetracycline, chloramphenicol, sulfonamides and the like; antimalarials such as 4-aminoquinolines, 8-aminoquinolines and pyrimethamine; hormonal agents such as prednisolone, cortisone, cortisol and triamcinolone; androgenic steroids, for example, methyltestosterone, fluoximesterone and the like; estrogenic steroids, for example, 17β-estradiol and ethinyl estradiol; progestational steroids, for example 17α-hydroxyprogesterone acetate, 19-nor-progesterone, norethindrone and the like; sympathomimetic drugs such as epinephrine, amphetamine, ephedrine, norepinephrine and the like; cardiovascular drugs, for example, procainamide, amyl nitrite, nitroglycerin, dipyridamole, sodium nitrate, mannitol nitrate and the like; diuretics, for example, chlorothiazide, flumethiazide and the like; antiparasitic agents such as bephenium hydroxynaphthoate and dichlorophen, dapsone and the like; neoplastic agents such as mechlorethamine, uracil mustard, 5-fluorouracil, 6-thioguanine, procarbazine and the like; hypoglycemic drugs such as insulins, protamine zinc insulin suspension, globin zinc insulin, isophane insulin suspension, and other art known extended insulin suspensions, sulfonylureas such as tolbutamide, acetohexamide, tolazamide, and chlorpropamide, the biguanides and the like; nutritional agents such as vitamins, essential amino acids, essential fats and the like; and other physiologically or pharmacologically active agents. Also, the drugs can be present as the pharmacologically acceptable derivatives, such as ethers, esters, amides, acetals, etc. that lend themselves to passage into the circulatory system. These derivatives can be prepared by art known techniques and then used in the practice of the invention. Of course, the drug derivative should be such as to convert to the active drug within the body through the action of body enzymes assisted transformations, pH, specific organ activities, and the like.

The amount of the drug present in the reservoir is generally non-limited and it is an amount equal to or larger than the amount of a drug that on its release form the reservoir is effective for bringing about the drug's physiological or pharmacological local or systemic effects. For example, the amount of drug present in the reservoir of a drug delivery device suitable for maintaining a supply of drug in the reservoir when the device is used for a period of time to achieve local or systemic effect is for various drugs, such as 11-desmethoxyreserpine about 5 to 40 mg in the reservoir; for acetophenazine an amount in the reservoir of 100 to 200 mg; for methoxypromizine about 600 to 750 mg in the reservoir; for emcylamate a reservoir amount of 1.5 to 2.0 gm; for phenylglycodol a reservoir amount of 1.5 to 1.9 gm; about 160 to 250 mg of butabarbital in the reservoir; about 150 to 170 mg of chlorodiazepoxide; from 0.5 to 1.2 gm of methsuximide; from 0.7 to 1.9 gm of ethosuximide; from 20 to 40 mg of hydrolazine, about 50 to 100 mg of totazoline; and the like.

It will be appreciated by those versed in the art that the unique drug delivery device of this invention can provide for the programmed delivery of drug at a rate of delivery characterized by a zero order time dependence for prolonged period of time; and, that the device therefore lends itself to administering an effective amount of drug needed for a therapeutic effect while essentially avoiding the presence of excessive amount of drug at the needed biological site. For example, the amount of drug in the reservoir can be 10 to 30 mg of thiopropzate for releasing 5 to 10 mg over a given time; 100 to 200 mg in the reservoir of phenyltoloxamine for a release of 50 mg; 100 to 200 mg of papaverine in the reservoir for a release of 30 to 75 mg over a determined time; 500 to 600 mg of mephenoxalone for a release of 375 to 425 mg; 15 to 25 mg of tranylcypromane for a release of 10 to 15 mg of a desired time span; 325 to 375 mg of trimethadione present in the reservoir for a release of 300 mg; 1 to 2 mg of dihydromorphinone for a release administration of 0.5 to 1.0 mg; rapid acting, intermediate acting and long acting insulins of zinc, globin, isophane, lente, and protamine types present in the reservoir for released administration of 10 to 20 U.S.P. administered three to four times per day for short acting, for intermediate 10 to 30 U.S.P. once or twice a day, and for long acting 10 to 50 U.S.P. once a day; prostaglandins for example $PGE_1$, $PGE_2$, $PGA_1$, $PGF_2$ in amounts of 0.5 mg to 10 mg for release of 1 ng to 100 ng and the like; for progestogen, progesterone an amount of 0.01 to 20 mg; and the like.

The above drugs and other drugs can be present in the reservoir alone or in combination form with pharmaceutical carriers. The pharmaceutical carriers acceptable for the purpose of this invention are the art known carriers that do not adversely affect the drug, the host or the material comprising the drug delivery device. Suitable pharmaceutical carriers include sterile wter; saline; dextrose; dextrose in water or saline; condensation products of castor oil and ehtylene oxide combining about 30 to about 35 moles of ethylene oxide per mole of castor oil; liquid glyceryl triester of a lower molecular weight fatty acid; lower alkanols; oils such as corn oil; peanut oil; sesame oil and the like with emulsifiers such as mono or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrrolidone); and the like, alone, or with suitable dispensing agents such as lecithin; polyoxyethylene stearate; and the like. The carrier may also contain adjuvants such as preserving, stabilizing, wetting, emulsifying agents, and the like.

The drug can also be mixed in the reservoir with a transporting agent, that is, a material that aids or a assists the puncturing projections of the drug delivery device to achieve the passage of the drug through the stratum corneum. The transporting aids suitable for the purpose of the invention are the therapeutically acceptable transporting aids that do not adversely affect the host, the drug or alter or adversely affect the materials forming the drug delivery device. The transporting aids can be used alone or they can be admixed with acceptable carriers and the like. Exemplary of transporting aids include monovalent, saturated and unsaturated aliphatic cycloaliphatic and aromatic alcohols having 4 to 12 carbon atoms, such as, hexanol, cyclohexane and the like; aliphatic cycloaliphatic and aromatic hydrocarbons having from 5 to 12 carbon atoms such as hexane, cyclohexane, isopropylbenzene and the like; cycloaliphatic and aromatic aldehydes and ketones having from 4 to 10 carbon atoms such as cyclohexanone; acetamide; N,N-di(lower)alkyl acetamides such as N,N-diethyl acetamide, N,N-diemthyl acetamide, N-(2-hydroxyethyl)acetamide, and the like; and other transporting agents such as aliphatic, cycloaliphatic and aromatic esters; essential oils; halogenated or nitrated aliphatic, cycloaliphatic and aromatic hydrocarbons; salicylates; polyalkylene glycol silicates; mixtures thereof; and the like.

The following examples are merely illustrative of the present invention and they should not be considered as limiting the scope of the invention in any way, as these examples and other equivalents thereof will become apparent to those versed in the art in the light of the present disclosure, drawings and the accompanying claims.

EXAMPLE 1

A drug is percutaneously administered by using one of the drug delivery devices of the invention as follows: first, a drug delivery device 10, as shown in FIG. 1, is positioned on the body surface where a preselected drug is to be administered for a local or systemic effect. Next, manual pressure, preferably by rotary or reciprocal forces, is applied to move the free, sharp end of puncturing projections 12 through the stratum corneum. Then, drug 20 in reservoir 16 passes through openings 11 into projections 12 and through projections 12, outward from openings 18 to the host just beneath the stratum corneum. Passage of drug out of reservoir 16 can be assisted by applying force to the rear wall of the reservoir. From there, the drug is absorbed through the interior layers of the skin and into the circulatory system.

EXAMPLE 2

A covered drug delivery device as shown in FIG. 6 is used as follows: first, the bandage covers 33 are peeled from the face of drug delivery device 10. Next, the device is positioned at the body site, where the drug is needed or is to be administered into the circulatory system, and pressure applied by means of the operator's fingers, not shown, to direct the puncturing projections 12 through the stratum corneum. Then, drug 20 diffusively exits reservoir 16 and moves through puncturing projections 12 and their apertures 18, when thusly equipped, to enter a host at a point beneath the stratum corneum. The adhesive 31 suitably provides a means for keeping the drug delivery system on the body for continuous delivery of a drug.

It will be obvious to those versed in the art in the light of the present specification, drawings and accompanying claims that the invention makes available to the art both a novel and useful drug delivery device for percutaneously administering a drug to produce a local or systemic effect. The device of the invention pioneers in contributing to the art both the means and method for the art to percutaneously administer a drug under controlled conditions through the epidermis which presents a surface area greater than other routes for drug absorption. The drug delivery device of the invention overcomes the barrier of the stratum corneum to penetration and thus makes it possible to administer smaller, and more effective dosage amounts of a drug for its local or systemic effect while simultaneously lessening or overcoming the undesirable effects frequently associated with larger doses of a drug, especially when drug is administered without the device or by other drug routes. The drug delivery device by percutaneously administering a drug followed by its absorption into the circulation, avoids the acidic and enzymatic actions of the gastrointestinal tract that often demands larger doses and also inherently makes oral administration impractical for certain drugs, for example, protein type drugs having a peptide linkage that are digested to inactive forms, and that can now be administered by the drug delivery device of the invention. Drug administration at a controlled and predetermined rate is made possible by this invention. For the rate of release of drug out of the device can be controlled by passage through interior passageways in the projections and/or by passage through a barrier of a drug release rate controlling material.

It will be further obvious to those versed in the art that many different embodiments of this invention can be made without departing from the spirit and scope of the invention. Accrodingly, it is to be understood that the invention is not to be construed as limited, but it embraces all equivalents inherent herein.

I claim:

1. A drug delivery device for percutaneously administering a drug comprising, a. a plurality of puncturing projections, formed of a drug release rate controlling material permeable to passage of a drug by diffusion, and b. a reservoir communicating with said projections containing the drug and whereby drug from the reservoir enters the projections and by diffusion through the projections is percutaneously administered through the stratum corneum of the epidermis.

* * * * *